United States Patent
Weeber et al.

(10) Patent No.: US 9,364,456 B1
(45) Date of Patent: Jun. 14, 2016

(54) KETONE ESTERS FOR TREATMENT OF ANGELMAN SYNDROME

(71) Applicants: Edwin John Weeber, Apollo Beach, FL (US); Stephanie Lynn Ciarlone, Bassett, VA (US); Dominic Paul D'Agostino, Tampa, FL (US)

(72) Inventors: Edwin John Weeber, Apollo Beach, FL (US); Stephanie Lynn Ciarlone, Bassett, VA (US); Dominic Paul D'Agostino, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 14/755,358

(22) Filed: Jun. 30, 2015

(51) Int. Cl.
*A61K 31/22* (2006.01)
*A61K 31/225* (2006.01)

(52) U.S. Cl.
CPC ............... *A61K 31/22* (2013.01); *A61K 31/225* (2013.01)

(58) Field of Classification Search
None
See application file for complete search history.

(56) References Cited

U.S. PATENT DOCUMENTS

| | | |
|---|---|---|
| 2014/0072654 A1 | 3/2014 | D'Agostino et al. |
| 2014/0073693 A1 | 3/2014 | D'Agostino et al. |

OTHER PUBLICATIONS

Blankenship, S.L. et al. "A ketone ester supplement improves specific phenotypes of the Angelman syndrome mouse model" poster presented at the Society for Neuroscience Annual Meeting, Nov. 16, 2014.
Blankenship, S.L. et al. "A ketone ester supplement improves specific phenotypes of the Angelman syndrome mouse model" poster presented at the University of South Florida Research Day, Feb. 20, 2015.
Clayton-Smith, J. and Laan, L. "Angelman syndrome: a review of the clinical and genetic aspects" *J. Med. Genet.*, 2003, 40(2):87-95.
D'Agostino, D.P. et al. "Therapeutic ketosis with ketone ester delays central nervous system oxygen toxicity seizures in rats" *Am. J. Physiol. Regul. Integr. Comp. Physiol.*, 2013, 304:R829-R836.
Evangeliou, A. et al. "Ketogenic diet in a patient with Angelman syndrome" *Pediatrics International*, 2010, 52(5):831-834.
Hashim, S. and Vanitallie, T. "Ketone body therapy: from the ketogenic diet to the oral administration of ketone ester" *J. Lipid Res.*, 2014, 55:1818-1826.
Jiang, Y-H. et al. "Mutation of the Angelman ubiquitin ligase in mice causes increased cytoplasmic p53 and deficits of contextual learning and long-term potentiation" *Neuron*, 1998, 21(4):799-811.
Kawamura, M. et al. "Ketogenic diet sensitizes glucose control of hippocampal excitability" *J. Lipid Res.*, 2014, 55:2254-2260.
Lossie, A.C. et al. "Distinct phenotypes distinguish the molecular classes of Angelman syndrome" *J. Med. Genet.*, 2001, 38(12):834-845.
Matsuura, T. et al. "De novo truncating mutations in E6-AP ubiquitin-protein ligase gene (*UBE3A*) in Angelman syndrome" *Nature Genetics*, 1997, 15:74-77.
Neal, E. "Ketogenic dietary therapy for epilepsy and other disorders: current perspectives" *Nutrition and Dietary Supplements*, 2014, 6:25-33.
Oh, J.S. et al. "Regulation of the neuron-specific Ras GTPase-activating protein, synGAP, by $Ca^{2+}$/calmodulin-dependent protein kinase II" *J. Biol. Chem.*, 2004, 279(17):17980-17988.
Song, B. et al. "PSD-95 promotes CaMKII-catalyzed serine phosphorylation of the synaptic RAS-GTPase activating protein SynGAP after transient brain ischemia in rat hippocampus" *Brain Res.*, 2004, 1005(1-2):44-50.
Thibert, R. et al. "Low glycemic index treatment for seizures in Angelman syndrome" *Epilepsia*, 2012, 53(9):1498-1502.
Trotter, J. et al. "Dab1 is required for synaptic plasticity and associative learning" *J. Neurosci.*, 2013, 33(39):15652-15668.
Varela, M.C. et al. "Phenotypic variability in Angelman syndrome: comparison among different deletion classes and between deletion and UPD subjects" *Eur. J. Human Genetics*, 2004, 12:987-992.
Weeber, E.J. et al. "Derangements of hippocampal calcium/calmodulin-dependent protein kinase II in a mouse model for Angelman mental retardation syndrome" *J. Neurosci.*, 2003, 23(7):2634-2644.
Williams, C.A. "Neurological aspects of the Angelman syndrome" *Brain & Devl.*, 2005, 27:88-94.
Williams, C.A. et al. "Angelman Syndrome 2005: Updated Consensus for Diagnostic Criteria" *Am. J. Med. Genetics*, 2006, 140A:413-418.

*Primary Examiner* — Samantha Shterengarts
(74) *Attorney, Agent, or Firm* — Saliwanchik, Lloyd & Eisenschenk

(57) ABSTRACT

The invention concerns a method of treating Angelman Syndrome (AS) in a subject, comprising inducing ketosis in the subject by administering a therapeutically effective amount of a ketone ester, such as an R,S-1,3-butanediol acetoacetate ester, wherein administration of the ketone ester elevates the blood ketone level in the subject. Other aspects of the invention include a method of increasing cognitive function and/or motor function in a subject with AS; and a method of decreasing seizures and increasing the latency to seize in a subject with AS.

18 Claims, 4 Drawing Sheets

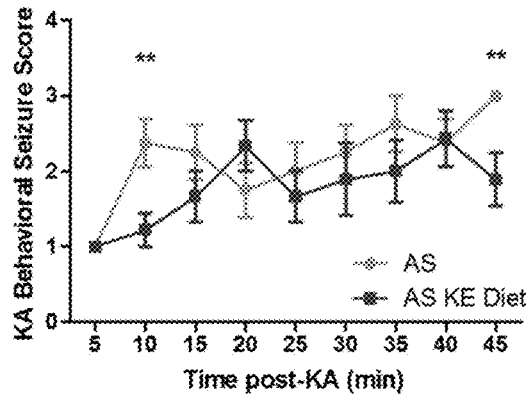
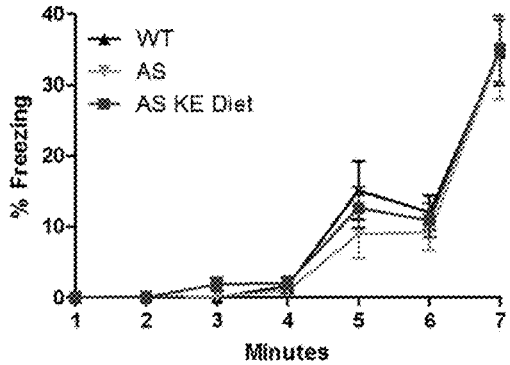
FIG. 7    FIG. 8
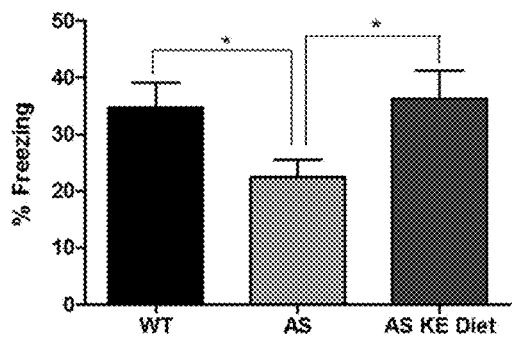
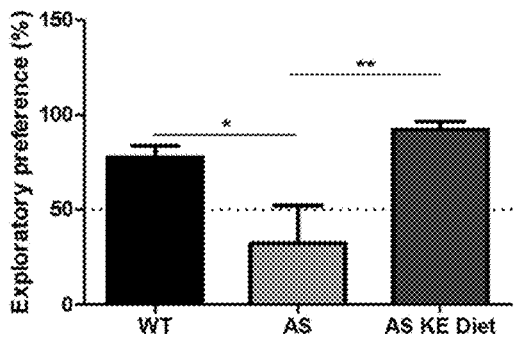
FIG. 9    FIG. 10
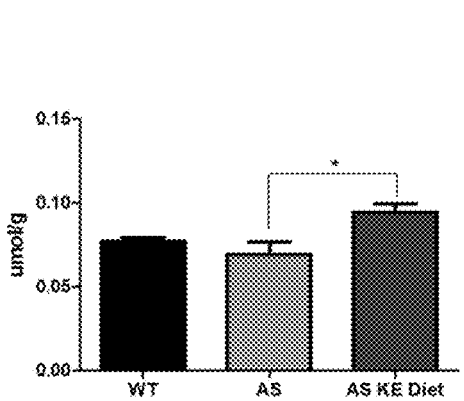
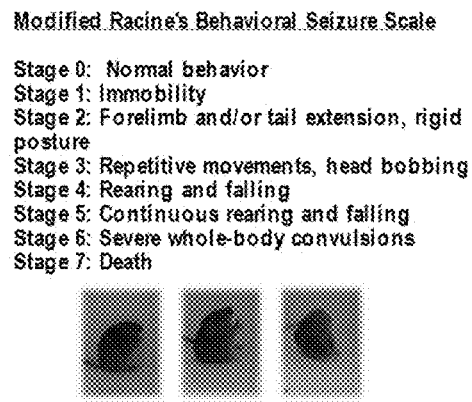
FIG. 11    FIG. 12

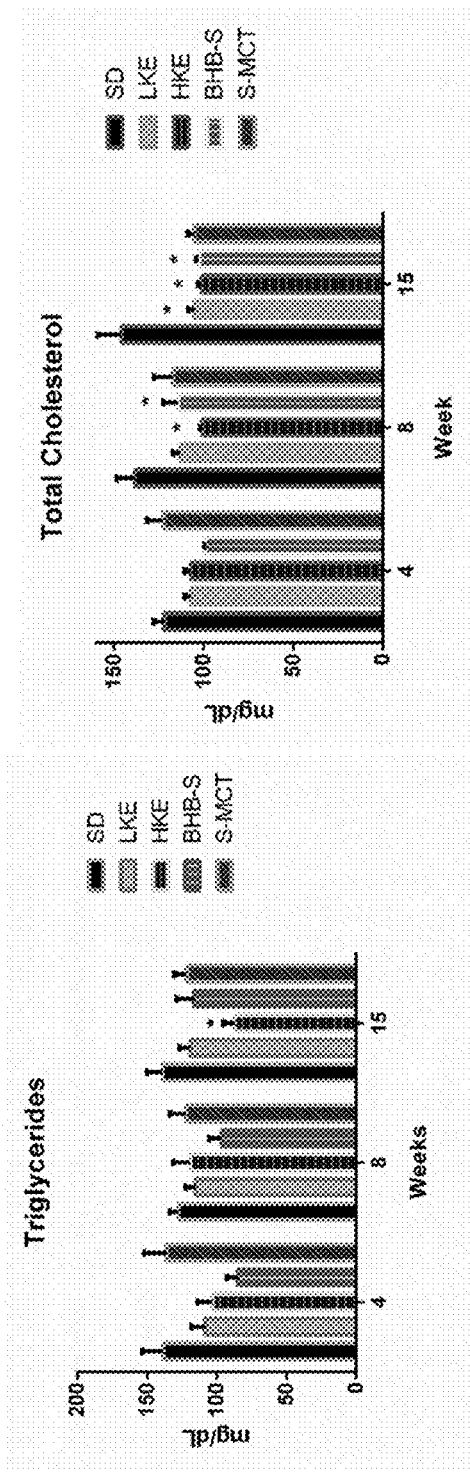
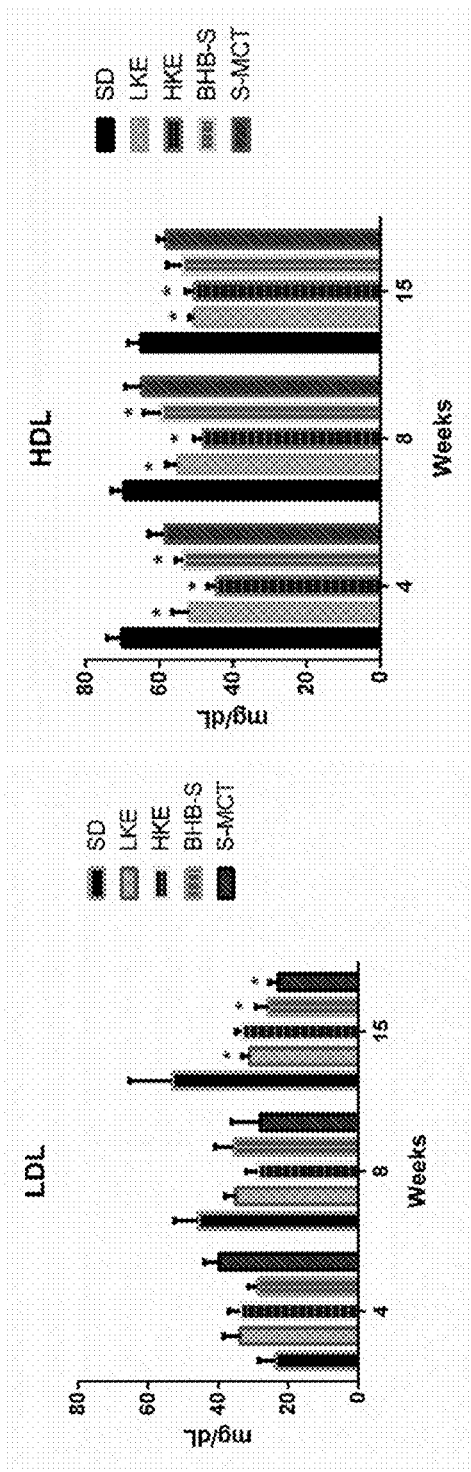
FIG. 15A
FIG. 15B
FIG. 15C
FIG. 15D

KETONE ESTERS FOR TREATMENT OF ANGELMAN SYNDROME

BACKGROUND OF THE INVENTION

Angelman Syndrome (AS) is a devastating neurological disorder with a prevalence of 1 in 15,000 that currently has no cure. AS presents with ataxia, frequent smiling, and laughter, lack of speech, and severe, debilitating seizures. Epilepsy in AS is often refractory to many prescribed medications, and frequently involves many seizure types. Furthermore, chronic, intractable epilepsy is shown to cause hippocampal damage and is associated with cognitive decline. The severity of seizures and lack of consistently effective anti-epileptic medications for AS patients demonstrates a considerable need for other therapeutic options.

Research in the AS field primarily focuses on finding an overall treatment for the disorder, without specific examination of the devastating epilepsy phenotype. Epilepsy is a common cause of death in AS and is present in over 80% of AS patients, with 77% of these patients remaining refractory. Unfortunately, common anti-epileptic drugs have serious adverse side effects, and there is limited data on alternative therapies, including dietary therapies.

BRIEF SUMMARY OF THE INVENTION

The present invention concerns methods for treating Angelman Syndrome (AS), comprising administering an effective amount of a ketone ester to a subject in need thereof. In some embodiments, the ketone ester is an orally administered dietary supplement, such as $BD-AcAc_2$.

Dietary therapeutic approaches can be especially problematic in patients suffering from AS. AS patients have accompanying gastrointestinal abnormalities, olfactory aversions, low body weight, and reduced muscle tone. Thus, the use of a ketone ester supplement may represent a more accessible and palatable method of inducing ketosis in AS patients.

The connection between abnormal electroencephalograms (EEG), seizure propensity, and cognitive disruption is unclear. The results described herein indicate that therapy with ketone esters can provide improvements in the seizure, motor, and cognitive phenotypes in AS. This therapy could help increase life expectancy and affect overall cognition, particularly if treatment is started early.

BRIEF DESCRIPTION OF THE DRAWINGS

FIG. 7. Kainic Acid Seizures. $BD-AcAc_2$ delays severity of kainic acid-induced seizures. AS treated mice displayed a significant decrease in behavioral seizure score compared to AS control mice at 10 and 45 minutes post-administration (Repeated measures ANOVA, Tukey's post-hoc tests, p<0.01).

FIG. 8. FC Training $BD-AcAc_2$ administration does not affect the fear conditioning training phase. There were no differences during the training phase of fear conditioning, indicating that all groups of mice were capable of freezing to the same extent.

FIG. 9. Contextual Fear Conditioning. $BD-AcAc_2$ administration improves hippocampal-dependent learning following contextual fear conditioning. AS mice show significant deficits in contextual fear conditioning when assessed 24 hours after training (Student's t-test, p<0.05). AS treated mice, however, froze at the same rate as the wild-type mice.

FIG. 10. Novel Object Recognition. $BD-AcAc_2$ administration enhances novel object recognition memory in AS mice. AS-treated and WT mice spend significantly more time with the novel object than AS treated animals (One-way ANOVA, Tukey's post-hoc test, p<0.05, p<0.01). Dotted line represents >50%, indicating intact recognition memory.

FIG. 11. Hippocampal GABA:Glutamate. TCA cycle intermediates are altered by ingestion of R,S-1,3-butanediol-diacetoacetate ester for 8 weeks in combination with a standard diet. The ratio of hippocampal GABA to glutamate is significantly increased in AS animals fed the ketone ester compared to AS animals fed only the standard diet (One-way ANOVA, p<0.05).

FIG. 12. Modified Racine's Behavioral Seizure Scale.

FIGS. 15A-15D. Chronic ketone supplementation lowered blood triglycerides, total cholesterol, LDL, and HDL.

DETAILED DESCRIPTION OF THE INVENTION

Figure 1:
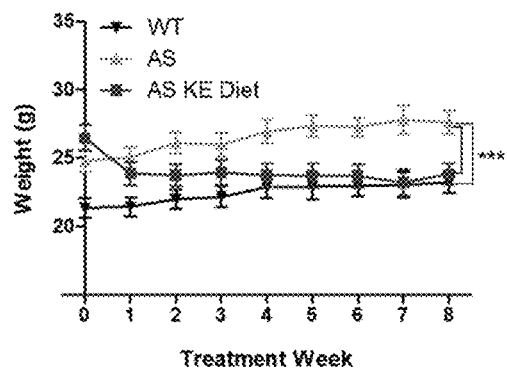
FIG. 1. Group Weights. $BD-AcAc_2$ normalizes body weight in AS mice. AS-treated mice displayed significantly decreased weight gain, similar to WT, compared to their AS controls (Repeated measures ANOVA, p<0.001).

Angelman Syndrome (AS) is associated with the deletion of chromosomal region 15q11-q13, and although the deletion overlaps with chromosomal deletions resulting in another form of mental retardation syndrome termed Prader Willi syndrome (PWS), AS occurs when the deletion is on a maternally inherited chromosome while PWS occurs when the deletion is on a paternally inherited chromosome. AS can be further classified based on various factors including the location of the cytogenetic abnormality (Lossie A C et al., *J Med Genet.,* 2001, December; 38(12):834-45; Clayton-Smith et al., *J Med Genet.,* 2003 February; 40(2):87-95; Varela M C et al., *Eur J Hum Genet.,* 2004 December, 12(12):987-92).

Molecular analysis indicates that the affected gene in one form of AS encodes an ubiquitin ligase, UBE3A, a protein involved in the ubiquitin mediated protein degradation pathway (Kishino T et al., *Nature Genetics,* 1997, 15:74-77). In the normal brain, the copy of UBE3A inherited from the father is nearly inactive through genetic imprinting such that the maternal copy performs most of the UBE3A function in the brain. Because of this imprinting phenomena, the AS phenotype is typically seen when the maternal copy is affected. Another form of AS is characterized by biparental inheritance of imprinted gene in the deleted region with a paternal only methylation pattern. The deleted region, termed IC, is hypothesized to act by resetting the male-female genomic imprint during oogenesis and the female-male imprint during spermatogenesis. Thus, the IC acts as a switch that turns on the maternal copy of UBE3A while silencing the paternal copy of the gene. Mutations and deletions in this critical region prevent the maternal to paternal imprinting switch in the AS families. Individuals with mutations in IC inherit the paternal imprint pattern on the mutant chromosome resulting in the inability to turn on the maternal UBE3A gene. Another form of AS is paternal uniparental disomy (UPD), in which the child inherits both copies of chromosome 15 from the father, with no copy inherited from the mother. In this case, there is no deletion or mutation, but the child is still missing the active UBE3A gene because the paternal-derived chromosomes only have brain-inactivated UBE3A genes. Those with the deletion type of AS are the most prevalent (about 70% of cases) and appear to have a more severe clinical phenotype (Williams C A, *Brain Dev.*, 2005 March, 27(2):88-94).

Mouse models of AS have been created by knockout of the corresponding mouse UBE3A gene. These animals show impairment of LTP, abnormal levels of p53 activity due to the reduction in its degradation by the ubiquitin pathway, and a dysregulation of CaMKII activity (Jiang Y H et al., *Neuron*, 1998, 21(4):799-811; Weeber E J et al., *J. Neurosci.*, 2003, 23(7):2634). Studies suggest an association between CaMKII activity and activation of Ras GTPase activating protein (Song B et al., *Brain Res.*, 2004, 1005(1-2):44-50; Oh J S et al., *J Biol Chem.*, 2004, 279(17):17980-8).

The inventors have investigated a novel therapeutic strategy for treatment of Angelman Syndrome (AS): the ketone ester supplement R,S-1,3-butanediol acetoacetate diester (BD-AcAc$_2$). This supplement is thought to increase the [GABA] to [glutamate] ratio, altering brain metabolism. Both the ketogenic diet, a high fat, low carbohydrate, moderate protein diet, and the low-glycemic index treatment diet of high fat and limited carbohydrates are described as well-tolerated and successful in case reports involving AS patients. The inventors hypothesized that supplemental ketone administration would decrease seizure frequency, increase seizure threshold, and improve hippocampal-dependent cognition and motor learning deficiencies seen in Ube3a-deficient mice. These mice were fed standard rodent chow, either with or without the ketone supplement ad libitum, for 8 weeks. It was found that a ketone ester supplement improves specific phenotypes in the AS mouse model.

It was hypothesized that the ketone ester supplement would decrease seizure frequency and increase seizure threshold. Additionally, as significant decreases in [GABA] or tonic inhibition have been observed in the cerebellum of both human and mouse AS brains, the inventors hypothesized that improvements in cerebellar tasks, such as in the rotarod, would be observed.

Aspects of the invention include a method of treating AS in a subject, a method of increasing cognitive function and/or motor function in a subject with (AS), and a method of decreasing seizures, increasing the latency to seize, and/or increasing the ratio of hippocampal gamma-amino butyric acid (GABA) to glutamate in a subject with AS. Each of the aforementioned methods comprises administering a therapeutically effective amount of a ketone ester to the subject. In some embodiments, the method comprises inducing ketosis in the subject by administering a therapeutically effective amount of the ketone ester, wherein administration of the ketone ester elevates the blood ketone level in the subject. Ketone esters and their administration are described in D'Agostino et al., U.S. Patent Publication No. 2014/0073693 (published Mar. 13, 2014), and D'Agostino et al., U.S. Patent Publication No. 2014/0072654 (published Mar. 13, 2014), which are each incorporated herein by reference in their entirety.

The subject to be treated may have a class of AS characterized by: (1) a large interstitial deletion of 15q11-q13; (2) paternal uniparental disomy (UPD) of chromosome 15; (3) an imprinting defect (ID); (4) a mutation in the E3 ubiquitin protein ligase gene (UBE3A); or (5) unidentified mechanism(s).

The subject to be treated may be virtually any age (e.g., infant, adolescent or pre-adolescent child, or adult). In some embodiments, the subject is a child between zero months and five years of age. In some embodiments, the subject is a child under five years of age. In some embodiments, the subject is a child 3 years old or younger.

Preferably, the subject has been diagnosed with AS by an appropriately licensed clinician prior to administration of the ketone ester. Diagnostic criteria for the disorder were initially established in 1995 in collaboration with the Angelman syndrome Foundation (USA), and these criteria underwent revision in 2005 (Williams C A et al., *Am. J. Med. Genet.*, 2006, A 140 (5):413-8, which is incorporated herein by reference in its entirety). Consistent clinical characteristics (100%) observed in AS include developmental delay, movement or balance disorder (usually ataxia of gait, and/or tremulous movement of limbs); behavioral uniqueness (any combination of frequent laughter/smiling, apparent happy demeanor; easily excitable personality, often with uplifted hand-flapping, or waving movements; hypermotoric behavior); and speech impairment (none or minimal use of words; receptive and non-verbal communication skills higher than verbal ones). Frequent clinical characteristics observed in AS (more than 80%) include delayed, disproportionate growth in head circumference (usually resulting in microcephaly by age 2 years), seizures, onset usually <3 years of age (seizure severity usually decreases with age but the seizure disorder lasts throughout adulthood), and abnormal EEG (with a characteristic pattern occurring in the first 2 years of life and can precede clinical features). The types of seizures include myoclonic ("jerks"), atonic or astatic ("drops"), and tonic ("stiffening") seizures.

In some embodiments, the subject is diagnosed with a specific class of AS prior to administration of the ketone ester (e.g., AS characterized by: (1) a large interstitial deletion of 15q11-q13; (2) paternal uniparental disomy (UPD) of chromosome 15; (3) an imprinting defect (ID); (4) a mutation in the E3 ubiquitin protein ligase gene (UBE3A); or (5) unidentified mechanism(s).

Optionally, the methods may further comprise evaluating the subject to assess the presence or absence of improvement in one or more symptoms or indicators of AS after one or more administrations of the ketone ester.

In some embodiments, the subject has one or more neurological disorders in addition to AS. In some embodiments, the subject has no neurological disorders other than AS.

In some embodiments, the subject has undergone a previous treatment for the AS (such as with an anti-epileptic drug). In some embodiments, the subject has undergone a previous treatment for the AS and epilepsy associated with the AS is refractory to the previous treatment.

In some embodiments, the subject is on a ketogenic diet at the time of administration of the ketone ester (see, for example, Evangeliou A et al., "Ketogenic diet in a patient with Angelman syndrome", *Pediatrics International*, 2010, 52 (5): 831-834, which describes a ketogenic diet and is incorporated herein by reference in its entirety). In some embodiments, the subject is not on a ketogenic diet.

Optionally, the ketone esters can be administered alone or in combination with one or more other medical or non-medical treatments. For example, one or more other therapeutic and/or prophylactic agents may be administered to a subject before, during, and/or after administration of the ketone ester. The other agent(s) may be administered to the subject within the same composition as the ketone ester or administered in a separate composition. For example, the other medical treatment(s) may be an anti-seizure agent (e.g., an anti-epileptic drug; AED), such as sodium valproate (e.g., Epilim), clonazepam (e.g., Rivotril, Epitril, Klonopin), lamotrigine (e.g., Lamictal), carbamazepine (e.g., Tegretol), levitiracetam (e.g., Keppra), piraqcetam (Nootropil), clobazam (e.g., Frisium, Onfri), diazepam (e.g., valium, diastat), divalproex (e.g., Depakote), eslicarbazepine acetate (e.g., Aptiom), ethosuximide (e.g., Zarontin), gabapentin (e.g., Neurontin, Gralise, Gabarone), Lacasamide (e.g., Vimpat), perampanel (e.g., Fycompa), phenobarbital, phenytoin (e.g., Dilantin, Phenytek), pregabalin (e.g., Lyrica), rufinamide (e.g., Banzel), Tiagabine hydrochloride (e.g., Gabitril), oxcarbazepine (e.g., Trileptal), Vigabatrin (e.g., Sabril), ezogabine (e.g., Potiga), felbamate (e.g., Felbatol), lorazepam (e.g., Ativan), primidone (e.g., mysoline), topiramate (e.g., Topamax), zonisamide (e.g., Zonegran), or valproic acid.

Other therapies may be agents that fully or partially restore function of the UBE3A gene. Other therapies may be provided to the subject such as physical therapy, occupational therapy, communication (e.g., speech) therapy, and/or behavioral therapy.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the terms "a" and "an" preceding an element or component of the invention are intended to be non-restrictive regarding the number of instances, i.e., occurrences of the element or component. Therefore, "a" or "an" should be read to include one or at least one, and the singular word form of the element or component also includes the plural unless the number is obviously meant to be singular.

As used herein, the term "patient" describes a human or non-human animal that may exhibit an AS phenotype and to whom treatment is administered, including prophylactic treatment with the compositions of the present invention. The terms "patient" and "subject" are used interchangeably herein.

As used herein, the term "ketosis" refers to an increase in ketone bodies in a subject. Ketosis is safe at levels below about 8 mM and these levels are referred to herein as a nonpathological "mild ketosis" or "therapeutic ketosis". Ketosis may be due to a ketogenic diet (1(D), starvation, or the administration of supplemental ketones (e.g., ketone esters).

The term "neurological disorders" as used herein refers to disorders of the central nervous system that are caused by disruptions of brain metabolism. These neurological disorders include, but are not limited to, seizure disorders, Alzheimer's disease, malignant brain cancer including glioblastomas, and traumatic brain injury.

As used herein, the terms "cancer", "tumor", "cancerous", and "malignant" refer to the physiological condition in humans and animals that is typically characterized by unregulated cell growth. Examples of cancer include, but are not limited to, brain cancer including tumors in neural tissue such as gliomas, glioblastomas, neuroblastomas, neuroepitheliomatous tumors, and nerve sheath tumors.

As used herein, the terms "administration" and "administering" are used to describe the process in which a composition, such as an individual ketone ester or any combination of ketone esters thereof, are delivered to a subject. The composition may be administered in various ways including oral (e.g., ingestion), intragastric, and parenteral (referring to intravenous and intra-arterial and other appropriate parenteral routes), among others. Each condition may be readily treated using other administration routes of ketone esters or any combination thereof to treat a disease or condition. Administration can be continuous or at distinct intervals, as can be determined by a person of ordinary skill in the art. In some embodiments, the ketone ester is administered enterally, ingested orally or by feeding tube, for example. Many AS babies have difficulty with breast or bottle feeding including problems of apparent uncoordinated sucking, tongue thrusting, and poor breast attachment.

The "therapeutically effective amount" for purposes herein is thus determined by such considerations as are known in the art. A therapeutically effective amount of individual ketone esters or any combination thereof is that amount necessary to provide a therapeutically effective result in vivo. The amount of ketone esters or any combination of ketone esters thereof must be effective to achieve a response, including but not limited to total prevention of (e.g., protection against) and to improved survival rate or more rapid recovery, or improvement or elimination of symptoms or other indicators of AS as are selected as appropriate measures by those skilled in the art. Symptoms or indicators of AS that may exhibit improvement in response to treatment include, but are not limited to, seizures, cognitive disruption, and motor deficiency. For example, improvement may be exhibited in the form of decreased seizure frequency, improved cognition, improved motor coordination, and improved learning and memory tasks.

In accordance with the present invention, a suitable single dose size is a dose that is capable of preventing or alleviating (reducing or eliminating) a symptom of AS in a patient when administered one or more times over a suitable time period. One of skill in the art can readily determine appropriate single dose sizes for systemic administration based on the size of a mammal and the route of administration.

The amount of the ketone ester will depend on absorption, distribution, metabolism, and excretion rates of the ketone ester as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The amount of the ketone esters administered to a subject may vary with the particular ketone ester, the method of administration, and the particular disorder being treated. The dose should be sufficient to affect a desirable response, such as a therapeutic or prophylactic response against a particular disorder or condition (e.g., Angelman Syndrome).

Specific esters, including an enriched BD-AcAc and a purified form of $BD-AcAc_2$, were previously developed. These esters can be used alone or in mixtures. BD-AcAc is relatively water soluble, whereas $BD-AcAc_2$ is poorly water soluble and lipophilic.

The BD-AcAc and $BD-AcAc_2$ are non-ionized sodium-free precursors of the ketone body acetoacetate. When ingested, these KEs are de-esterified in the blood and tissues by esterase enzymes and release acetoacetate in a rapid and sustained process. The resulting R,S-1,3 butanediol is a common food additive that breaks down to beta-hydroxybutyrate. The metabolic fate of R,S-1,3 butanediol involves alcohol dehydrogenase, which catalyzes the initial step in metabolism of 1,3-butanediol to beta-hydroxybutyraldehyde, which is rapidly oxidized to beta-hydroxybutyrate by aldehyde dehydrogenase. Subsequent metabolic steps to acetoacetate and acetyl CoA supplies substrate for the Krebs cycle (tricarboxylic-acid cycle) to produce carbon dioxide and reducing equivalents (that are converted to ATP by the electron transport chain).

While ketone esters can be administered as isolated compounds, these compounds can also be administered as part of a composition. The subject invention thus further provides compositions comprising one or more ketone esters in association with at least one pharmaceutically acceptable carrier.

The ketone esters and compositions containing them can be formulated according to known methods for preparing pharmaceutically useful compositions. Formulations are described in a number of sources which are well known and readily available to those skilled in the art. For example, *Remington's Pharmaceutical Science* (Martin 1995) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

The ketone ester can be formulated in a composition for administration to a subject as an edible solid (e.g., a nutraceutical bar or beverage), or as an oral solid, semi-solid, or liquid pharmaceutical composition, such as a tablet (e.g., flash, chewable, buccal, sublingual, effervescent, or simply swallowed), capsule (hard-shelled or soft-shelled), pill, granules, powder (bulk powder or divided powder), oral suspension, syrup, elixir, oral drops, emulsion (oil-in-water or water-in-oil), pastilles, lozenge. Other dosage forms that may be utilized include injection (intravenous, intramuscular, subcutaneous); transdermal ointment, cream, gel (jelly), and paste; suppository; enema; pessary; inhaled dosage form (e.g., with inhaler or nebulizer); eye drops, ophthalmic ointment or gel; and nasal drops or sprays. The ketone ester may be formulated for immediate release, delayed release, or sustained release.

EXEMPLIFIED EMBODIMENTS

Examples of embodiments of the invention include, but are not limited to:

Embodiment 1

A method of treating Angelman Syndrome (AS) in a subject, comprising administering a therapeutically effective amount of a ketone ester to the subject.

Embodiment 2

The method of embodiment 1, wherein the ketone ester is derived from acetoacetate (AcAc).

Embodiment 3

The method of embodiment 1 or 2, wherein the ketone ester is a R,S-1,3-butanediol acetoacetate ester.

Embodiment 4

The method of any preceding embodiment, wherein the ketone ester is R,S-1,3-butanediol acetoacetate monoester, R,S-1,3-butanediol acetoacetate diester ($BD-AcAc_2$), or a combination of both.

Embodiment 5

The method of any preceding embodiment, wherein the subject is a child under five years of age.

Embodiment 6

The method of any preceding embodiment, further comprising administering an anti-seizure agent.

Embodiment 7

The method of any preceding embodiment, wherein the subject has previously been treated for the AS with an anti-seizure agent and has refractory epilepsy.

Embodiment 8

A method of increasing cognitive function and/or motor function in a subject with Angelman Syndrome (AS), comprising administering a therapeutically effective amount of a ketone ester to the subject.

Embodiment 9

The method of embodiment 8, wherein the ketone ester is derived from acetoacetate (AcAc).

Embodiment 10

The method of embodiment 8 or 9, wherein the ketone ester is a R,S-1,3-butanediol acetoacetate ester.

Embodiment 11

The method of any preceding embodiment, wherein the ketone ester is R,S-1,3-butanediol acetoacetate monoester, R,S-1,3-butanediol acetoacetate diester (BD-AcAc$_2$), or a combination of both.

Embodiment 12

The method of any preceding embodiment, wherein the subject is a child under five years of age.

Embodiment 13

The method of any preceding embodiment, further comprising administering an anti-seizure agent.

Embodiment 14

The method of any preceding embodiment, wherein the subject has previously been treated for the AS with an anti-seizure agent and has refractory epilepsy.

Embodiment 15

A method of decreasing seizures, increasing the latency to seize, and/or increasing the ratio of hippocampal gamma-amino butyric acid (GABA) to glutamate in a subject with Angelman Syndrome (AS), comprising inducing ketosis in the subject by administering a therapeutically effective dose of a ketone ester, wherein administration of the ketone ester elevates the blood ketone level in the subject.

Embodiment 16

The method of embodiment 15, wherein the ketone ester is derived from acetoacetate (AcAc).

Embodiment 17

The method of embodiment 15 or 16, wherein the ketone ester is a R,S-1,3-butanediol acetoacetate ester.

Embodiment 18

The method of any preceding embodiment, wherein the ketone ester is R,S-1,3-butanediol acetoacetate monoester, R,S-1,3-butanediol acetoacetate diester (BD-AcAc$_2$), or a combination of both.

Embodiment 19

The method of any preceding embodiment, wherein the subject is a child under five years of age.

Embodiment 20

The method of any preceding embodiment, further comprising administering an anti-seizure agent.

Embodiment 21

The method of any preceding embodiment, wherein the subject has previously been treated for the AS with an anti-seizure agent and has refractory epilepsy.

Following are examples that illustrate procedures for practicing the invention. These examples should not be construed as limiting. All percentages are by weight and all solvent mixture proportions are by volume unless otherwise noted.

Materials and Methods

Mice.

Mice with the UBE3A null mutation (AS) were described previously (Jiang Y H et al., *Neuron*, 1998, 21(4):799-811). All experiments were performed on mice that have been backcrossed to the C57BL/6 line (Jackson Labs, Bar Harbor, Me.) for at least 5 generations. Female C57BL/6 mice containing the null mutation were bred with C57BL/6 (WT) males to produce maternally-deficient AS offspring and WT littermate controls. Audiogenic seizure experiments were performed on mice with the 129/SvEv background, with the same breeding scheme as the C57BL/6 mice. Animals were kept on a 12 hour light-dark cycle and food and water provided ad libitum. All animal testing procedures were approved by the Institutional Animal Care and Use Committee of the University of South Florida and followed the NIH guidelines for the care and use of laboratory animals.

Ketone Ester Administration.

Control mice received standard rodent chow fed ad libitum. Mice receiving the ketone supplement were administered BD-AcAc$_2$ with their standard rodent chow ad libitum. These mice received standard rodent chow mixed at 10% BD-AcAc$_2$ and 1% saccharin by volume.

Blood Glucose and Ketone Levels.

Blood was collected from the tip of the tail weekly using the Precision Xtra system with both glucose and ketone test strips, each requiring 0.6 µL samples.

Kainic Acid Injections.

Mice were injected with 20 mg/kg of kainic acid i.p. and were monitored for seizure activity for 45 minutes and behavioral seizure score was recorded (modified Racine's scale).

Induced Audiogenic Seizures.

Seizures were induced by exposing mice to a 120-dB white noise in a sound-attenuated chamber until seizures occurred or for a maximum of 60 s. Both seizure frequency and threshold (time until seizures began) were recorded.

Behavioral Testing:

Rotarod Testing.

Mice were placed on a rotating rod (Rotarod, Ugo Basile, Italy) that accelerated from 4 to 40 rpm. For two consecutive days, four trials were performed per day with a 45-60 min interval between trials. The maximum duration of each trial was 5 minutes. The time that the mice fell off the rod was recorded. Data analysis was performed by using two-way ANOVA (genotype×trials) with repeated measures.

Associative Fear Conditioning.

Fear conditioning was used to assess hippocampal function and associative learning and memory. Training included 2 shock-tone (CS/US) pairings. Detailed methods have been previously described (Trotter, J. et al., *The Journal of Neuroscience*, 2013, 33(39):315652-15668). For the context test, 24 hours following CS/US pairing mice were placed back into the chamber and allowed to explore for 3 minutes.

Novel Object Recognition.

Novel object recognition was used to evaluate recognition memory. Following habituation to an open field arena, mice were allowed to explore the arena containing two identical objects for 15 minutes. 24 hours following training, a novel object replaced one of the old objects and mice were allowed to explore for 5 minutes.

Metabolic Analysis of TCA Cycle Intermediates.

Brains were dissected and immediately frozen in liquid nitrogen within 30 seconds of removal and stored at −80° C.

Hippocampal sections were then homogenized and spiked with the appropriate internal standards. Homogenates were extracted and the derivatized products were measured under GC-MS. A DB-17 MS capillary column was used in all analysis. Ions for glutamate and GABA were monitored and data acquisition collected and stored for further analysis.

Statistical Analysis.

Data are shown as the mean±SEM, and analyzed by Student's t-test or ANOVA. Tukey's post hoc test was used where appropriate. Statistical significance was determined when $p<0.05$.

Example 1

Ketone Esters Decrease Audiogenic Seizures and Increase Latency to Seize

Ube3a-deficient mice were fed standard rodent chow, either with or without the ketone supplement (BD-AcAc$_2$) ad libitum, for 8 weeks. The inventors hypothesized that supplemental ketone administration would decrease seizure frequency, increase seizure threshold, and improve hippocampal-dependent cognition and motor learning deficiencies.

Figure 2:
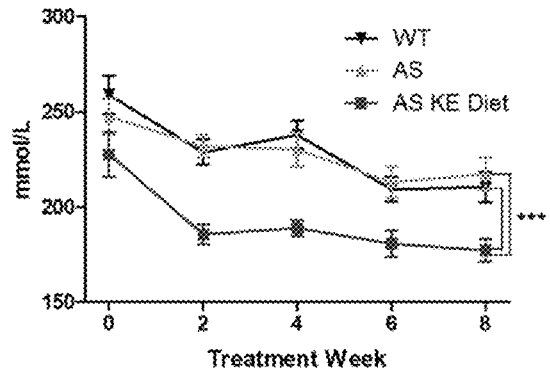
FIG. 2. Glucose Levels. Decreased glucose in AS animals fed the KE diet. AS mice fed the KE diet demonstrated decreased blood glucose compared to WT and AS mice fed the control diet (Repeated measures ANOVA, p<0.001).
Figure 3:
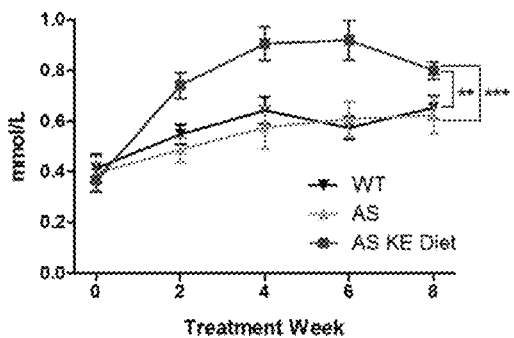
FIG. 3. Ketone Levels. Elevated ketones in AS animals fed the KE diet. AS mice fed the KE diet demonstrated elevated ketones compared to WT and AS controls (Repeated measures ANOVA WT compared to AS treated, p<0.01, AS compared to AS treated, p<0.001).
Figure 4:
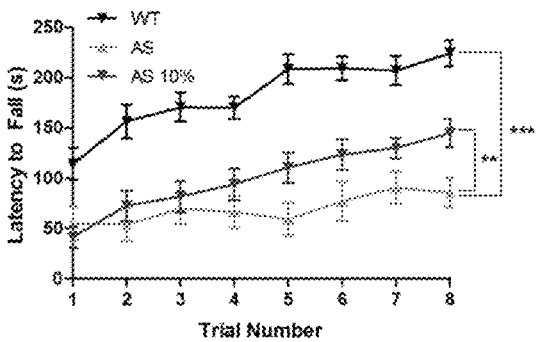
FIG. 4. Rotarod. $BD-AcAc_2$ administration increases rotarod performance in AS mice. WT mice remained on the rotarod significantly longer than their AS littermates (Repeated measures ANOVA, p<0.001). AS treated mice also show increased rotarod performance compared to their AS littermate controls (Repeated measures ANOVA, p<0.01).
Figure 5:
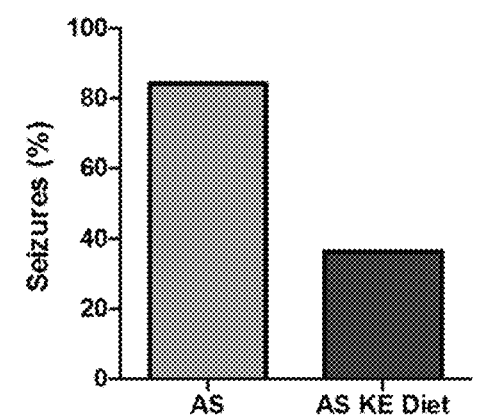
FIG. 5. Audiogenic Seizure Frequency. The ketone ester decreases seizure activity in AS mice after 8 weeks on the diet. Categorical data shows a decrease in seizure frequency in the AS treated group (86%) compared to the AS control diet group (37%).
Figure 6:
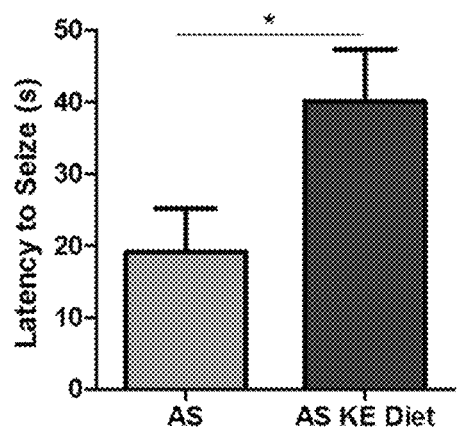
FIG. 6. Latency to Seize. $BD-AcAc_2$ increases latency to seize in AS mice. AS treated mice displayed a significant increase in the latency to seize compared to AS control mice (Student's t-test, p<0.05).

The ketone ester supplement normalizes weight, decreases blood glucose, and increases blood ketone levels in Ube3a-deficient mice, indicating the diet is altering metabolism. Mice fed the ketone ester supplement demonstrated improvements in both motor coordination and learning and memory tasks, suggesting cognitive and motor function may be enhanced in AS-treated mice (FIGS. 1-3). Audiogenic seizures were decreased and latency to seize was increased in AS-treated animals, suggesting the use of the ketone ester as an anticonvulsant (FIGS. 5 and 6). GABA:Glutamate was significantly increased in AS treated animals, indicating these TCA cycle intermediates have been altered by the diet (FIG. 11).

Improvements were observed in multiple phenotypes of the UBE3A-deficient mice. Thus, the ketone supplement improves motor coordination and associative learning, decreases seizure frequency, and increases seizure threshold in AS mice. UBE3A m-/p+ mice have previously demonstrated significantly decreased tonic inhibition in the cerebellum. Therefore, increasing GABA:Glutamate via the ketone ester may dampen overall neuronal excitability and increase the signal-to-noise ratio, improving motor function output and decreasing seizure frequency.

Example 2

Safety of Ketone Esters for Oral Chronic Administration

Male Sprague Dawley rats (N=10/group) were fed ad libitum (approximate dose based on food intake recorded during study) for the study duration (15 weeks).

TABLE 1

Chronic Feeding of Ketone Supplements

| Tx | Agent | % in Diet | Approx. Dose |
|---|---|---|---|
| SD | Standard Rodent Chow | — | — |
| LKE | Ketone Ester (low dose) | 5% | 10 g/kg/day |
| HKE | Ketone Ester (high dose) | 20% | 25 g/kg/day |
| BHB-S | Na$^+$/Ca$^{+2}$ βHB Salt | 20% | 25 g/kg/day |
| S-MCT | 1:1 βHB Salt : MCT Oil | 20% | 25 g/kg/day |

Figure 13:
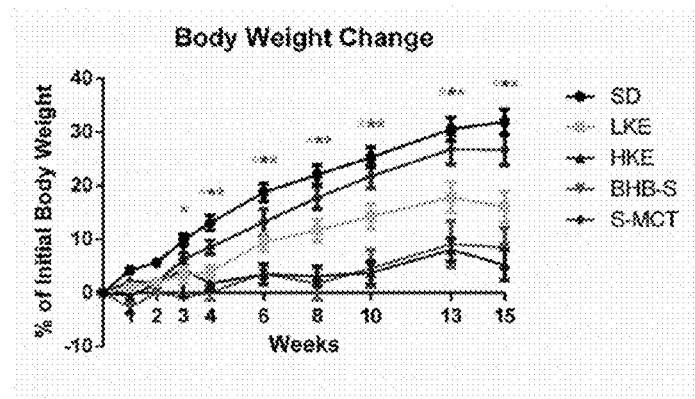
FIG. 13. Chronic ketone supplementation slowed weight gain over time.

Measured Parameters:
Weight
Food/calorie intake
Blood glucose
Blood ketones
Triglycerides
Total Cholesterol
HDL
LDL
Safety/toxicity—serum clinical chemistry tests for kidney and liver function Inflammatory Profile:

Chronic ketone supplementation slowed weight gain over time (FIG. 13).

Rats consuming the KE and S/MCT ketone supplements adjusted food consumption to regulate caloric intake to a large extent, while BHB-S treated rats restricted caloric intake (FIG. 13).

Figure 14A:
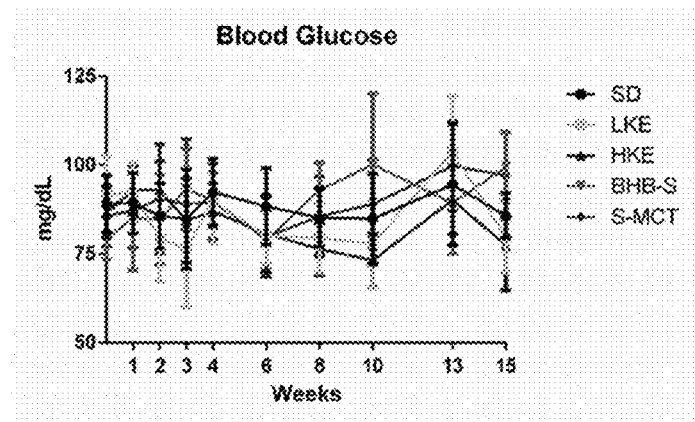
FIGS. 14A and 14B. Chronic ketone supplementation elevated blood ketones without significantly affecting blood glucose levels.
Figure 14B:
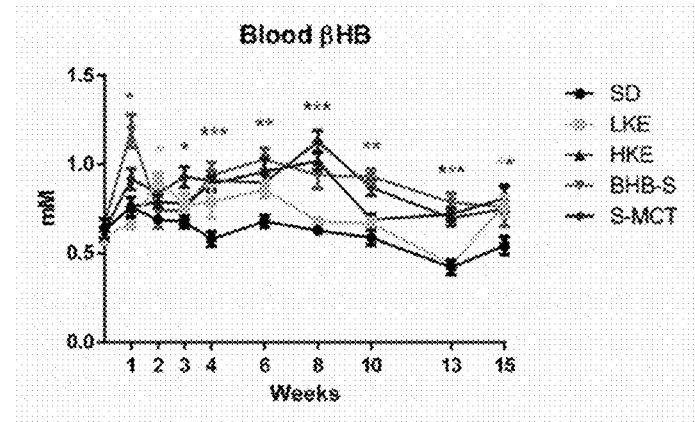

Approximate caloric intake compared to controls following adaptation to diet (weeks 13-15):
  LKE: +10% kcal
  HKE: −7% kcal
  BHB/S: −25% kcal
  S/MCT: −8.8% kcal Chronic ketone supplementation elevated blood ketones without significantly affecting blood glucose levels (FIGS. 14A and 14B).

Chronic ketone supplementation lowered blood triglycerides, total cholesterol, LDL, and HDL (FIGS. 15A-15D).

Preliminary studies suggest that chronic consumption of high doses of ketone supplements are not toxic to the kidneys or liver.

Serum clinical chemistry analysis did not reveal any changes in major markers of kidney or liver function such as BUN, creatinine, total protein, albumin, globulin, bilirubin, ALT, ALP, or GGT compared to control, SD-fed rats.

TABLE 2

| Serum Marker | LKE | HKE |
|---|---|---|
| Blood Urea Nitrogen (BUN) | ns | Ns |
| Creatinine | ns | Ns |
| Phosphorous | ns | Ns |
| Calcium | ns | Ns |
| Total Protein | ns | Ns |
| Albumin | ns | Ns |
| Globulin | ns | Ns |
| Glucose | ns | Ns |
| Cholesterol | ns | Ns |
| Alanine Aminotransferase (ALT) | ns | Ns |
| Alkaline Phosphatase (ALP) | ns | Ns |
| Gamma Glutamyltransferase (GGT) | ns | Ns |
| Total Bilirubin | ns | Ns |
| Sodium | ns | Ns |
| Potassium | ns | Ns |
| Chloride | ns | Ns |

(ns = no change from control)

Chronic ketone supplementation altered the serum inflammatory profile. Preliminary analysis suggests that chronic ketone supplementation may elicit an anti-inflammatory response as it lowered the production of several pro-inflammatory cytokines, such as IL-1b, IL-6, IFN-γ, MCP-1, and RANTES and increased the production of the anti-inflammatory cytokine VEGF.

Fractalkine, a pro-inflammatory cytokine that also plays a role in synaptic plasticity in the hippocampus, was increased.

TABLE 3

| Cytokine/Chemokine | Change from Control | | | |
|---|---|---|---|---|
| | LKE | HKE | BHB-S | S/MCT |
| G-CSF | — | ↓T | ↓T | — |
| Eotaxin | ↓T | ↓** | ↓* | ↓T |
| GM-CSF | — | — | — | — |
| IL-1a | — | ↓* | — | — |
| Leptin | — | ↓* | ↓** | — |
| MIP-1a | ↑T | — | ↓* | — |
| IL-4 | — | — | ↓T | — |
| IL-1b | — | ↓* | — | — |
| IL-2 | — | ↓T | ↓T | — |
| IL-6 | ↓T | ↓* | ↓* | — |
| IL-13 | ↓T | ↓** | ↓T | — |
| IL-10 | — | ↓T | — | — |
| IL-12(p70) | ↓* | ↓* | ↓** | ↓T |
| IFNy | — | ↓* | ↓T | — |
| IL-5 | — | ↓* | — | — |
| IL-17a | — | — | — | — |
| IL-18 | — | ↓T | ↓T | — |
| MCP-1 | — | ↓T | — | — |
| IP-10 | — | ↓*** | — | — |
| GRO/KC | — | ↓T | — | — |
| VEGF | ↑* | — | — | — |
| Fractalkine | ↑** | ↑* | ↓T | — |
| LIX | — | ↓* | — | — |
| MIP-2 | — | — | — | ↓* |
| TNF-a | — | — | — | — |
| RANTES | — | ↓** | — | — |

↑: Increased from control
↓: Decreased from control
—: no change
T: Trend towards significance
*p < 0.05; p < 0.01; *p < 0.001

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of treating Angelman Syndrome (AS) in a subject, comprising inducing ketosis in the subject by administering a therapeutically effective amount of a ketone ester to the subject.

2. The method of claim 1, wherein the ketone ester is derived from acetoacetate (AcAc).

3. The method of claim 1, wherein the ketone ester is a R,S-1,3-butanediol acetoacetate ester.

4. The method of claim 3, wherein the ketone ester is R,S-1,3-butanediol acetoacetate monoester, R,S-1,3-butanediol acetoacetate diester (BD-AcAc$_2$), or a combination of both.

5. The method of claim 1, wherein the subject is a child under five years of age.

6. A method of increasing cognitive function and/or motor function in a subject with Angelman Syndrome (AS), comprising inducing ketosis in the subject by administering a therapeutically effective amount of a ketone ester to the subject.

7. The method of claim 6, wherein the ketone ester is derived from acetoacetate (AcAc).

8. The method of claim 7, wherein the ketone ester is a R,S-1,3-butanediol acetoacetate ester.

9. The method of claim 8, wherein the ketone ester is R,S-1,3-butanediol acetoacetate monoester, R,S-1,3-butanediol acetoacetate diester (BD-AcAc$_2$), or a combination of both.

10. The method of claim 6, wherein the subject is a child under five years of age.

11. A method of decreasing seizures, increasing the latency to seize, and/or increasing the ratio of hippocampal gamma-amino butyric acid (GABA) to glutamate in a subject with Angelman Syndrome (AS), comprising inducing ketosis in the subject by administering a therapeutically effective dose of a ketone ester, wherein administration of the ketone ester elevates the blood ketone level in the subject.

12. The method of claim 11, wherein the ketone ester is derived from acetoacetate (AcAc).

13. The method of claim 11, wherein the ketone ester is a R,S-1,3-butanediol acetoacetate ester.

14. The method of claim 11, wherein the ketone ester is R,S-1,3-butanediol acetoacetate monoester, R,S-1,3-butanediol acetoacetate diester (BD-AcAc$_2$), or a combination of both.

15. The method of claim 11, wherein the subject is a child under five years of age.

16. The method of claim 1, wherein the ketone ester is administered orally as a solid, semi-solid, or liquid composition that is consumed by the subject.

17. The method of claim 6, wherein the ketone ester is administered orally as a solid, semi-solid, or liquid composition that is consumed by the subject.

18. The method of claim 11, wherein the ketone ester is administered orally as a solid, semi-solid, or liquid composition that is consumed by the subject.

* * * * *